(12) United States Patent
Kim et al.

(10) Patent No.: US 9,605,015 B2
(45) Date of Patent: Mar. 28, 2017

(54) POLYENE COMPOUND, METHOD FOR PREPARING THE SAME, AND ANTIFUNGAL DRUG COMPRISING NOVEL POLYENE COMPOUND AS ACTIVE INGREDIENT

(75) Inventors: Eung-Soo Kim, Seoul (KR); Kyu Boem Han, Daejeon (KR); Shuangjun Lin, Shanghai (CN); Dekun Kong, Shanghai (CN); Linquan Bai, Shanghai (CN); Zixin Deng, Shanghai (CN); David H. Sherman, Ann Arbor, MI (US); Mi-Jin Lee, Incheon (KR)

(73) Assignee: INHA-INDUSTRY PARTNERSHIP INSTITUTE, Incheon (KR)

( * ) Notice: Subject to any disclaimer, the term of this patent is extended or adjusted under 35 U.S.C. 154(b) by 0 days.

(21) Appl. No.: 14/369,869

(22) PCT Filed: Aug. 31, 2012

(86) PCT No.: PCT/KR2012/007000
§ 371 (c)(1),
(2), (4) Date: Jun. 30, 2014

(87) PCT Pub. No.: WO2013/100315
PCT Pub. Date: Jul. 4, 2013

(65) Prior Publication Data
US 2014/0371436 A1  Dec. 18, 2014

(30) Foreign Application Priority Data

Dec. 30, 2011 (KR) .................. 10-2011-0147050

(51) Int. Cl.
| | | |
|---|---|---|
| C07H 15/26 | (2006.01) | |
| C12P 19/62 | (2006.01) | |
| C07H 17/08 | (2006.01) | |
| C07D 493/08 | (2006.01) | |

(52) U.S. Cl.
CPC ........... *C07H 17/08* (2013.01); *C07D 493/08* (2013.01); *C07H 15/26* (2013.01); *C12P 19/62* (2013.01)

(58) Field of Classification Search
CPC ................................ C07H 17/08; C12P 19/62
See application file for complete search history.

(56) References Cited

U.S. PATENT DOCUMENTS

| | | |
|---|---|---|
| 6,664,241 B2 | 12/2003 | Chang et al. |
| 2004/0266008 A1 | 12/2004 | Bachmann et al. |
| 2010/0286077 A1* | 11/2010 | Zotchev .................. C07H 1/00 514/31 |

FOREIGN PATENT DOCUMENTS

WO   WO-2013/100315 A1   7/2013

OTHER PUBLICATIONS

"International Application Serial No. PCT/KR2012/007000, International Search Report mailed Feb. 26, 2013", (w/ English Translation), 6 pgs.
Bierman, M., et al., "Plasmid cloning vectors for the conjugal transfer of DNA from *Escherichia coli* to *Streptomyces* spp.", *Gene*, 116(1), (1992), 43-49.
Bruheim, Per, et al., "Chemical Diversity of Polyene Macrolides Prodiced by *Streptomyces noursei* ATCC 11455 and Recombinant Strain ERD44 with Genetically Altered Polyketide Synthase NysC", *Antimicrob. Agents Chemother.*, 48(11), (2004), 4120-4129.
Kim, Byung-Gyun, et al., "Identification of functionally clustered nystatin-like biosynthetic genes in a rare actinomycetes, *Pseudonocardia autotrophica*", *J. Ind. Microbiol. Biotechnol.*, 36(11), (2009), 1425-1434.
Lee, Mi-Jin, et al., "Structural analysis and biosynthetic engineering of a solubility-improved and less-hemolytic nystatin-like polyene in *Pseudonocardia autotrophica*", *Appl. Microbiol. Biotechnol.*, 95(1), (2012), 157-168.
MacNeil, Douglas J., et al., "Analysis of *Streptomyces avermitilis* genes required for avermectin biosynthesis utilizing a novel integration vector", *Gene*, 111(1), (1992), 61-68.
Preobrazhenskaya, Maria N., et al., "Chemical Modification and Biological Evaluation of New Semisynthetic Derivatives of 28,29-Didehydronystatin $A_1$(S44HP), a Genetically Engineered Antifungal Polyene Macrolide Antibiotic", *J. Med. Chem.*, 52(1), (2009), 189-196.

\* cited by examiner

*Primary Examiner* — Shaojia Anna Jiang
*Assistant Examiner* — Bahar Craigo
(74) *Attorney, Agent, or Firm* — Schwegman Lundberg & Woessner, P.A.

(57) ABSTRACT

The present invention relates to a novel polyene compound similar to nystatin, a method for preparing the same, and an antifungal drug comprising the novel polyene compound as an active ingredient. Compared to nystatin comprising one sugar, NNP, which is the polyene compound similar to nystatin, displays 300 times higher solubility and ten times lower cytotoxicity while maintaining antifungal activity, and thus can be useful in developing a novel polyene antifungal agent having improved solubility and less toxicity in terms of pharmacokinetics.

4 Claims, 13 Drawing Sheets

POLYENE COMPOUND, METHOD FOR PREPARING THE SAME, AND ANTIFUNGAL DRUG COMPRISING NOVEL POLYENE COMPOUND AS ACTIVE INGREDIENT

RELATED APPLICATIONS

This application is a nationalization under 35 U.S.C. §371 from International Application Serial No. PCT/KR2012/007000, filed Aug. 31, 2012 and published as WO 2013/100315 A1 on Jul. 4, 2013, which claims the priority benefit of Korean Application Serial No. 10-2011-0147050, filed Dec. 30, 2011, the contents of which applications and publication are incorporated herein by reference in their entirety.

TECHNICAL FIELD

The present invention relates to a novel polyene compound similar to nystatin with improved solubility and less hemolytic activity which is prepared by the biological process, a method for preparing the same, and an antifungal drug comprising the novel polyene compound as an active ingredient.

BACKGROUND ART

Fungi are the typical eukaryotes having the nuclei and organelles. When fungi invade in the skin tissue, it causes Dermatomycoses. When fungi invade in the human body via the lung, that is, when they infect our body, they cause various diseases such as systemic mycoses and opportunistic mycoses particularly in those people whose immunity has been weakened, for example those with AIDS or with organ transplantation, etc.

Even though the necessity of antifungal agents for the treatment of the said diseases has been well understood, the medicine on the market to treat systemic infection is rare. Recently an antifungal agent targeting a specific component of cell wall, for example echinocandins, has been developed. However, most drugs including amphotericin B, azole containing nystatin, and polyene, are targeting the whole structure of fungal membrane.

The azole antifungal drugs have been widely used because they have less side effects. However, according to the recent increase of azole resistant fungi and the increased incidence rate of the infection by such resistant fungi, the treatment of the disease is in trouble, requiring the development of a new antifungal agent.

Polyenes are very interesting polykotone macrolide drugs that demonstrate active antifungal activity. These compounds include macrolactone rings having multiple conjugated double bonds that form a chromophore showing a characteristic spectrum in ultraviolet/visible ray region.

The antifungal activity of such antifungal agents as nystatin and amphotericin B is induced by the interaction between polyene molecules and the membrane comprising sterol. This interaction forms an ion channel and the membrane is now permeable therefore to destroy electrochemical gradient, leading to the death of the fungal cell. The said compounds have a great affinity rather to those membranes containing ergosterol (the major sterol found on the membranes of fungi and parasites such as *Trypanosoma* and *Leishmania*) than to those membranes containing cholesterol (mammalian cells). However, the interaction between polyene molecules and the membrane containing cholesterol is not meaningless, either. Owing to the side effects such as hemolytic activity along with low-solubility, these compounds do not satisfy the treatment of systemic fungal infection as a whole. Particularly, there is no better alternative than the polyene compounds to fight with fungal infection.

To overcome the problems of the conventional antifungal agents, the present inventors judged that the polyene compounds such as amphotericin B and nystatin would be clinically more practical than the azole compounds. Therefore, the present inventors tried to find out a novel polyene antifungal compound. As a result, the present inventor completed this invention by identifying a novel polyene compound having antifungal activity which also displayed improved solubility and less hemolytic activity while retaining antifungal activity.

DISCLOSURE

Technical Problem

It is an object of the present invention to provide a novel polyene compound similar to nystatin with improved solubility and less hemolytic activity while retaining antifungal activity.

It is another object of the present invention to provide a method for preparing the polyene compound similar to nystatin with improved solubility and less hemolytic activity while retaining antifungal activity by the biological process.

It is also an object of the present invention to provide an antifungal drug comprising the novel polyene compound similar to nystatin with improved solubility and less hemolytic activity while retaining antifungal activity as an active ingredient.

Technical Solution

Hereinafter, the present invention is described in detail.

The present invention provides the polyene compound represented by the following formula 1:

[Formula 1]

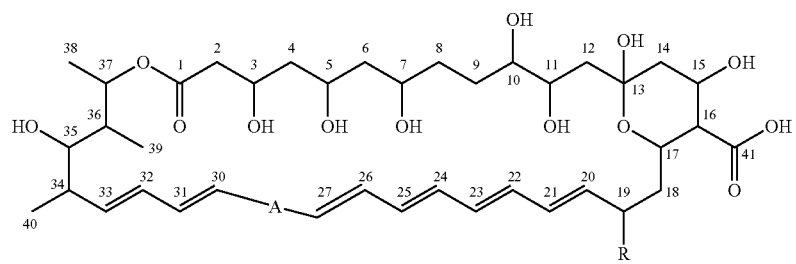

In the above formula,

A is $C_2$ alkylene or alkenyl group,

R can contain 2-5 homo- or heterosaccharides prepared by glycosidic linkage of one or more saccharides selected from the group consisting of mycosamine, glucosamine, N-acetylglucosamine, galactosamine, N-acetylgalactosamine, fucose, glucose, galactose, mannose, and fructose.

R can be mycosaminyl-($\alpha$1-4)-N-acetyl-glucosamine. Therefore, the polyene compound represented by formula 1 of the present invention is preferably the polyene compound represented by the following formula 2:

[Formula 2]

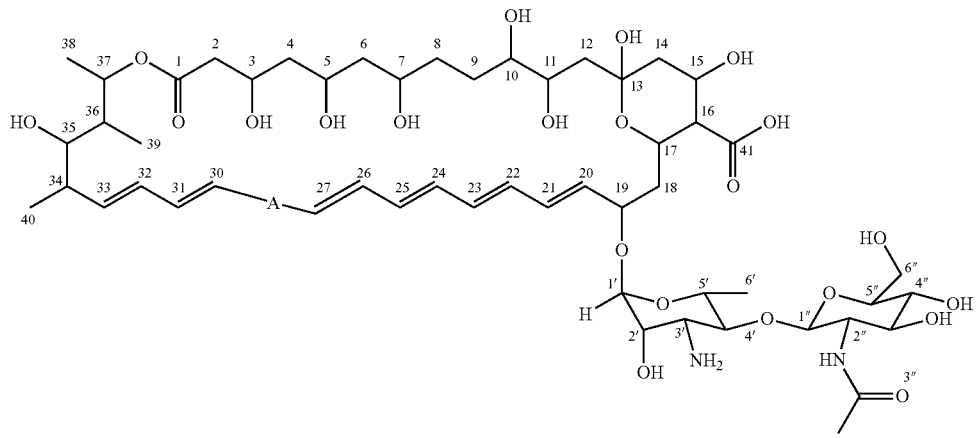

More preferably, the polyene compound represented by formula 1 of the present invention is the polyene compound represented by the following formula 3 or formula 4, but not always limited thereto.

[Formula 3]

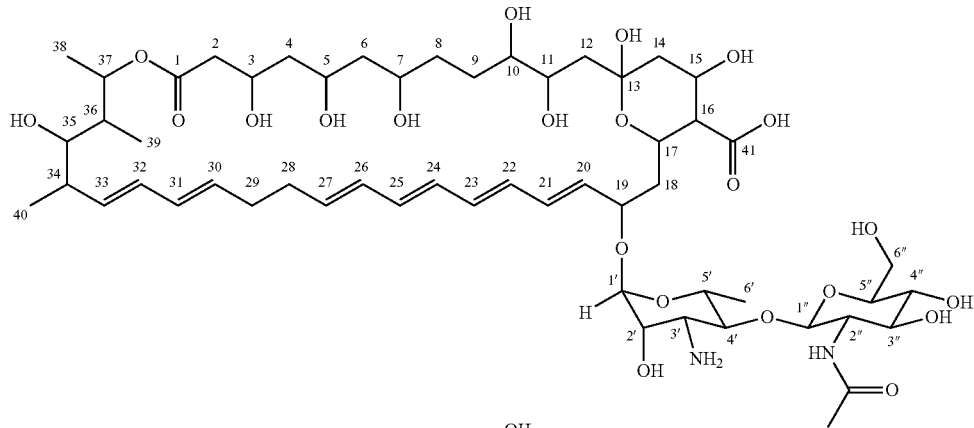

[Formula 4]

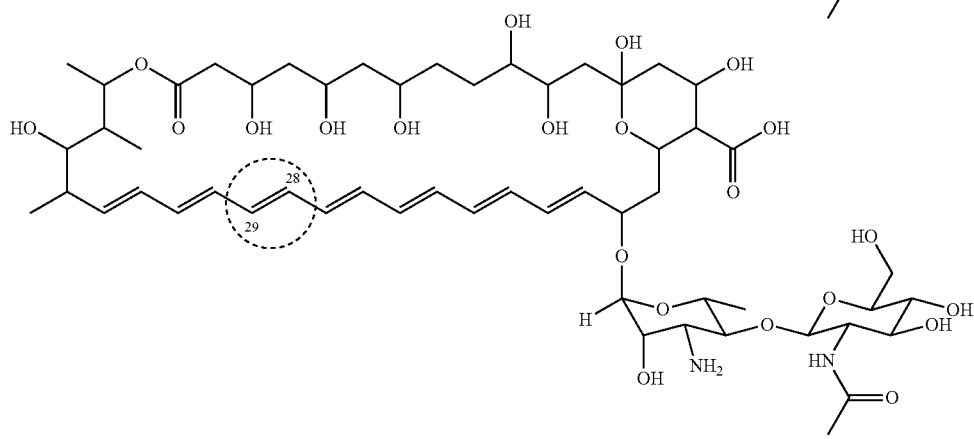

The polyene compound represented by formula 1 of the present invention can be isolated and purified from *Pseudonocardia autotrophica* KCTC9441 strain, and can be synthesized by all the conventional synthesis methods.

The present invention also provides a method for preparing the polyene compound represented by formula 1 by using *Pseudonocardia autotrophica*.

nysDI, the glyosyltransferase genes, necessary for the biosynthesis of Nystatin-like *Pseudonocardia* Polyene (NPP) can be used.

To prepare the polyene compound represented by formula 4, the strain is preferably the one with the deletion of enoyl reductase 5 (ER5) of nppC polyketide synthase (PKS) gene.

[Formula 1]

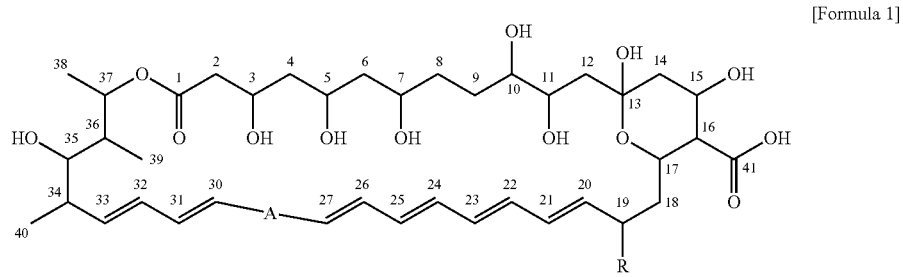

In the above formula,

A is $C_2$ alkylene or alkenyl group,

R can contain 2-5 homo- or heterosaccharides prepared by glycosidic linkage of one or more saccharides selected from the group consisting of mycosamine, glucosamine, N-acetylglucosamine, galactosamine, N-acetylgalactosamine, fucose, glucose, galactose, mannose, and fructose.

R can be mycosaminyl-($\alpha$1-4)-N-acetyl-glucosamine.

Particularly, the said method can include the step of separating the polyene compound of the invention from the strain culture obtained by culturing *Pseudonocardia autotrophica*.

The method can be one of the methods well-informed and generally used for the extraction and separation of a compound from a strain, and be performed singly or together with other methods. If necessary, the compound can be purified more precisely by the conventional method well known to those in the art.

In a preferred embodiment of the present invention, the polyene compound of the invention is prepared by the method comprising the following steps:

1) culturing a *Pseudonocardia autotrophica* strain;
2) extracting the strain culture obtained in step 1) by using an organic solvent; and
3) separating the organic solvent extract obtained in step 2) by column chromatography.

Particularly, the *Pseudonocardia autotrophica* strain of step 1) is preferably KCTC9441, but not always limited thereto, and any strain that is able to express nppDI and The nutrition source for the strain can be any conventional nutrition source generally used as a strain culture fluid. For example, as a carbon source, glucose, sucrose, starch syrup, dextrin, starch, and molasses can be used. As a nitrogen source, yeast extract, ammonium sulfate, sodium nitrate, and urea can be used. If necessary, common salt, potassium, magnesium, cobalt, chlorine, phosphate, sulfate, and other inorganic salts accelerating ion production can be added. The culture can be performed by shaking culture or stationary culture in aerobic condition preferably at 20-37° C. and more preferably at 25-30° C., but not always limited thereto.

In step 2), the polyene compound of the present invention can also be found not only in the culture fluid but also in the mycelium. Therefore, an active ingredient is extracted from the culture solution and/or the mycelium by adding an organic solvent such as butanol to the culture solution and/or the mycelium, followed by concentrating the active ingredient via vacuum evaporation, but not always limited thereto.

Step 3) is to separate the polyene compound of the present invention. The organic solvent extract obtained in step 2) proceeded to silica gel column chromatography using methanol:water mixed solvent, followed by high performance liquid chromatography. As a result, the purified novel polyene compound represented by formula 1 of the present invention is obtained.

In addition, the present invention provides an antifungal agent comprising the polyene compound represented by formula 1 as an active ingredient.

[Formula 1]

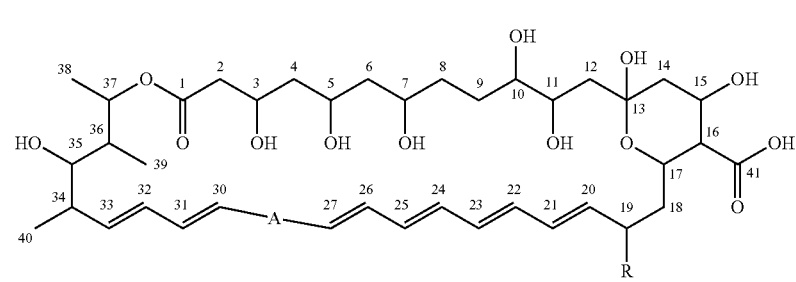

In the above formula,

A is $C_2$ alkylene or alkenyl group,

R can contain 2-5 homo- or heterosaccharides prepared by glycosidic linkage of one or more saccharides selected from the group consisting of mycosamine, glucosamine, N-acetylglucosamine, galactosamine, N-acetylgalactosamine, fucose, glucose, galactose, mannose, and fructose.

Based on the fact that polyene antibiotics such as nystatin are a large family of very valuable antifungal polyketide compounds typically produced by soil actinomycetes, the present inventors have attempted to develop a polyene compound having the similar structure to that of the above. As a result, the present inventors confirmed that *Pseudonocardia autotrophica* KCTC9441 could produce the novel compound NPP and the said NPP contained an aglycone identical to nystatin and harbored a unique di-sugar moiety, mycosaminyl-($\alpha$1-4)-N-acetyl-glucosamine (see FIG. 1*a* and FIG. 1*c*).

When nppDI, the sole glycosyltransferase encoding gene within the npp gene cluster, was inactivated, aglycone was synthesized (see Compound 3 of FIG. 1*a*). And this mutant could be functionally complemented in trans either by nppDI or its nystatin counterpart, nysDI. This result indicates that two sugars might be attached to the aglycone by two independent glycosyltransferases (see FIG. 1*a* and FIG. 5). In the meantime, when the ER5 domain of the nppC gene in the *Pseudonocardia autotrophica* strain was inactivated, the novel heptaene NPP derivative was synthesized (see FIG. 1*c* and FIG. 6).

The novel NPP of the present invention obtained above was confirmed to have 300 times higher solubility but 10 times lower hemolytic activity (cytotoxicity) than nystatin containing one sugar with maintaining antifungal activity (see FIG. 7 and FIG. 8).

Previous studies reported that the compound having heptaene structure had significantly higher antifungal activity than the compounds not having the structure (Bruheim P. et al., Antimicrob Agents Chemother 48:4120-4129). At this time, the number of conjugated double bonds is the reason of antifungal activity of the pharmacokinetically improved polyene. Therefore, the heptaene NPP derivative of the present invention also has high solubility but lower cytotoxicity with maintaining excellent antifungal activity.

Thus, the novel polyene compound of the present invention can be effectively used for the development of a novel polyene antifungal agent with pharmacokinetically improved solubility but less cytotoxicity.

The dose and the application method of the antifungal agent of the present invention can be varied with the formulation and the purpose of use.

The antifungal agent of the present invention is preferably included in the pharmaceutical composition of the invention at the concentration of 0.1-50 weight % by the total weight of the composition.

The antifungal agent of the present invention can additionally include proper carriers, excipients and diluents generally used for the preparation of a pharmaceutical composition. The carriers, excipients and diluents are exemplified by lactose, dextrose, sucrose, sorbitol, mannitol, xylitol, erythritol, maltitol, starch, acacia rubber, alginate, gelatin, calcium phosphate, calcium silcate, cellulose, methyl cellulose, microcrystalline cellulose, polyvinyl pyrrolidone, water, methylhydroxybenzoate, propylhydroxybenzoate, talc, magnesium stearate and mineral oil.

The antifungal agent of the present invention can be formulated for oral administration, for example powders, granules, tablets, capsules, suspensions, emulsions, syrups and aerosols, and for parenteral administration, for example external use, suppositories and sterile injections, etc.

The antifungal agent of the present invention can be prepared for oral or parenteral administration by mixing with generally used diluents or excipients such as fillers, extenders, binders, wetting agents, disintegrating agents and surfactant. Solid formulations for oral administration are tablets, pills, powders, granules and capsules. The solid formulations for oral administration are prepared by mixing one or more suitable excipients such as starch, calcium carbonate, sucrose or lactose, gelatin, etc.

Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations, suppositories and injections. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The effective dosage of NPP of the present invention can be determined according to the age, gender, and weight of a patient. The effective dosage is preferably 0.001-100 mg/kg per day, and more preferably 0.01-10 mg/kg per day. The administration frequency can be once a day or a few times a day. The actual dosage of NPP can be increased or decreased according to the administration pathway, the severity of a disease, and the age, gender, and weight of a patient. The above dosage cannot limit the scope of the invention in any way.

The antifungal agent of the present invention can be administered to rats, mice, cattle and mammals including human by various pathways, for example the possible administration pathway can be oral administration, rectal administration, intravenous injection, intramuscular injection, hypodermic injection, intrauterine injection or intracerebroventricular injection.

Advantageous Effect

According to the present invention, NPP, the polyene compound similar to nystatin, displays 300 times higher solubility and ten times lower cytotoxicity while maintaining antifungal activity, compared to nystatin comprising one sugar, and thus can be useful in developing a novel polyene antifungal agent having improved solubility and less toxicity in terms of pharmacokinetics.

DESCRIPTION OF DRAWINGS

The application of the preferred embodiments of the present invention is best understood with reference to the accompanying drawings, wherein:

FIG. 2 illustrates the inactivation of nppDI gene in *Pseudonocardia autotrophica*.

FIG. 3 illustrates the complementation of nppDI gene in the ESK601 mutant with nppDI and nysDI.

FIG. 4 illustrates the inactivation of the ER5 domain of nppC gene in *Pseudonocardia. autotrophica*.

BEST MODE

Figure 1A:
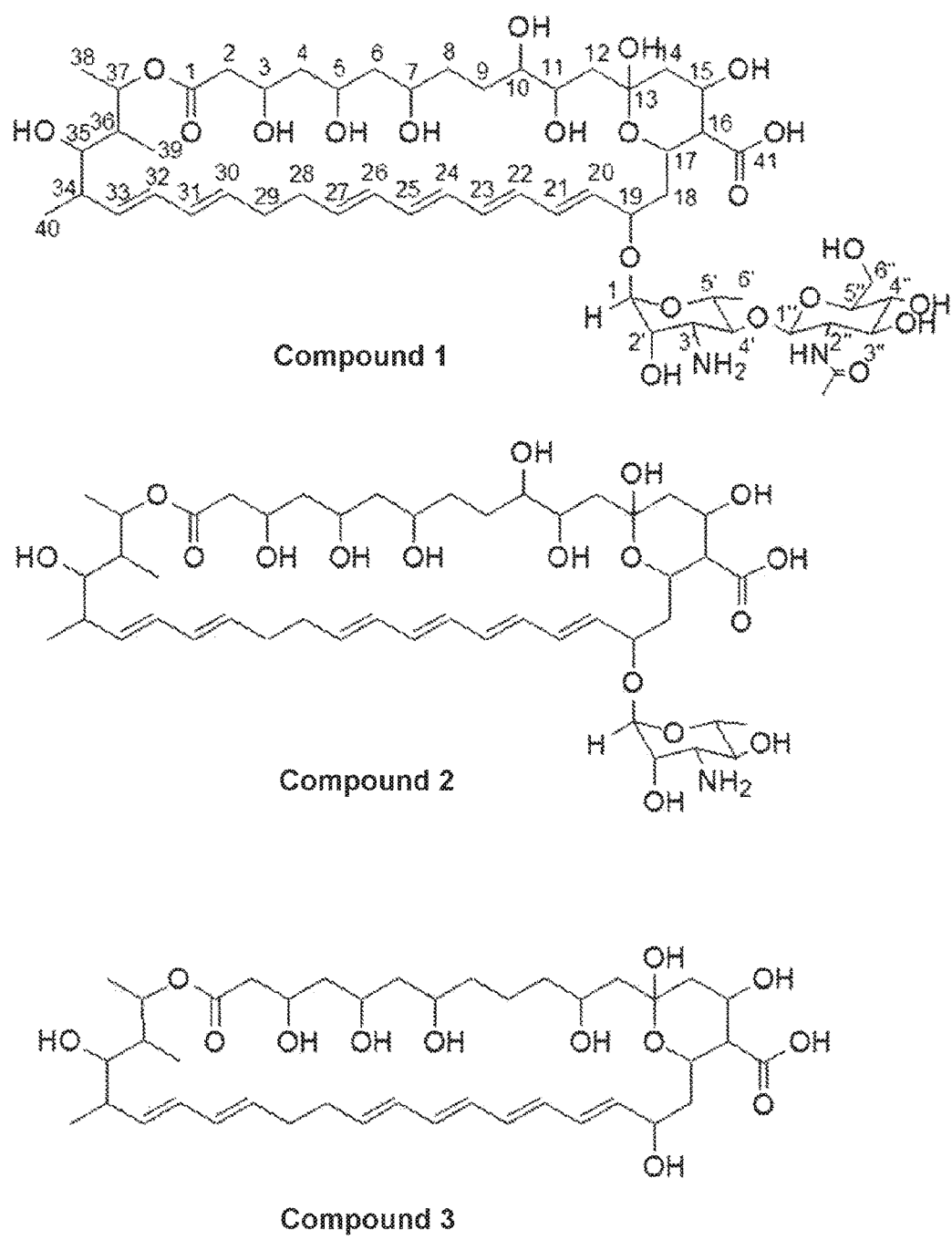
FIG. 1 illustrates the structures of natural NPP-related products. 1 of FIG. 1*a* indicates NPP, 2 indicates nystatin A1, and 3 indicates the structures of the compounds accumulated from the ESK601 mutants.
FIG. 1b illustrates the important $^1$H-$^1$H correlation and long-range $^1$H-$^{13}$C correlations.
FIG. 1c illustrates the structures of the compounds accumulated from the ESK604 mutants.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of Bacterial Strains, Plasmids, Growth Conditions, and DNA Manipulation In this example, the bacterial strains and plasmids shown in Table 1 were used.

TABLE 1

| Strain, plasmid Strain | Characteristics | Origin |
| --- | --- | --- |
| *Escherichia coli* | | |
| DH5α | Cloning host | |
| ET12567/pUZ8002 | Strain for intergeneric conjugation; Km$^r$, Cm$^r$ | Gene.111:61-68, 1992 |

TABLE 1-continued

| Strain, plasmid Strain | Characteristics | Origin |
| --- | --- | --- |
| *Pseudonocardia autotrophica* | | |
| KCTC9441 | Wild type, NPP producer | KCTC |
| ESK601 | ΔnppDImutant | |
| ESK602 | nppDI-complemented ESK601 | |
| ESK603 | nysDI-complemented ESK601 | |
| ESK604 | ΔER5mutant | |
| Fungi | | |
| *Candida albicans* ATCC10231 | Yeast-like fungi | ATCC |
| Recombinant plasmid | | |
| T&A cloning vector | General cloning plasmid | Real Biotech Corporation |
| pKC1139-tsr | *E. coli-P.autotrophica* conjugative vector, atemperature-sensitive suicide vector, Apr$^r$, Thio$^r$ | J Ind.Microbiol .Biot.36:1425-1434, 2009 |
| ermE*pSET152 | *E. coli-P. autotrophica* conjugative vector | Gene.116:43-49, 1992 |
| pMJDI | nppDI replacement vector | |
| pMJC5 | ER5 replacement vector | |
| pMJPDI | Vector for nppDIcomplementation, Hyg$^r$ | |
| pMJYDI | Vector for nysDIcomplementation, Hyg$^r$ | |

The *Pseudonocardia autotrophica* strain was cultured in ISP medium 2 (glucose 0.4%, yeast extract 0.4%, malt extract 1%, agar 2%) at 30° C. for sporulation. *Pseudonocardia autotrophica* spores were re-suspended, and stored in a sterile 20% glycerol solution at −20° C.

To isolate the total DNA, the spore suspension was inoculated in 25 ml of YEME liquid medium, followed by culture at 30° C. for 2 days. The method to isolate the total DNA used in this example was the conventional method known to those in the art (Genetic Manipulation of *Streptomyces*; A Laboratory Manual. The John Innes Foundation, Norwich, 1985).

All the *Escherichia coli* strains were cultured in LB (Luria-Bertani) broth or on LB agar supplemented with the appropriate antibiotics at 37° C. General techniques for DNA manipulation were used as described (Molecular Cloning; A laboratory manual, Cold Spring Harbor Laboratory Press, Cold Spring Harbor, N.Y., 1989). Isolation of the DNA fragments from *E. coli* and agarose gel was conducted using a LaboPass Kit (Cosmo Genetech, Korea). Oligonucleotide primers were purchased from Cosmo Genetech and their sequences are listed in Table 2. The DNA sequence of the NPP biosynthetic gene cluster was reported previously (J. Ind. Microbiol. Biot. 36:1425-1434, 2009).

TABLE 2

| Oligo-nucleotide | Sequence[a] | Restriction site | SEQ. ID. No. |
|---|---|---|---|
| DI.N.F | 5'-GGATCCGGTCGAACAGCGTG-3' | BamH I | 1 |
| DI.N.R | 5'-ACTAGTCTGATCCTGCGCCT-3' | Spe I | 2 |
| DI.A.F | 5'-ACTAGTACCCGTCGCGTGGCGC-3' | Spe I | 3 |
| DI.A.R | 5'-GGTACCGCTGATCCCGAACGA-3' | Kpn I | 4 |
| DI.checkF | 5'-TGACGTAGTCGAGCTCGT-3' | | 5 |
| DI.checkR | 5'-ATCAACTACCTGATCGCT-3' | | 6 |
| PDI.comp.F | 5'-AGATCTACCGAGGACTAGGGATT-3' | Bgl II | 7 |
| PDI.comp.R | 5'-TCTAGATGACTCCCTGGTTCGGT-3' | Xba I | 8 |
| YDI.comp.F | 5'-GGATCCACGGGCATTG GCCACA-3' | BamH I | 9 |
| YDI.comp.R | 5'-TCTAGAGTCAGTCGGTTGCCAGG-3' | Xba I | 10 |
| Comp.checkF | 5'-TGCAGCTGGCACGACAGG-3' | | 11 |
| ER5.AT.F | 5'-TCGAGTCCTGGGGGATCCGT-3' | BamH I | 12 |
| ER5.DH.R | 5'-CCGTGTCGGTACCTTCACCGT-3' | Kpn I | 13 |
| ER5.ER.F | 5'-GTGGGTACCCGCTGCCGGT-3' | Kpn I | 14 |
| ER5.KS.R | 5'-AGCCCTCTCTAGAGTCGCC-3' | Xba I | 15 |
| ER5.checkF | 5'-ACTGTTCGCGCTCGACTGGAC-3' | | 16 |
| ER5.checkR | 5'-TGGTCAGCAGCAGATGCCGCA-3' | | 17 |

[a]restriction site

EXAMPLE 2

Construction of nppDI Deletion Mutant *Pseudonocardia autotrophica* ESK601

Figure 2A:
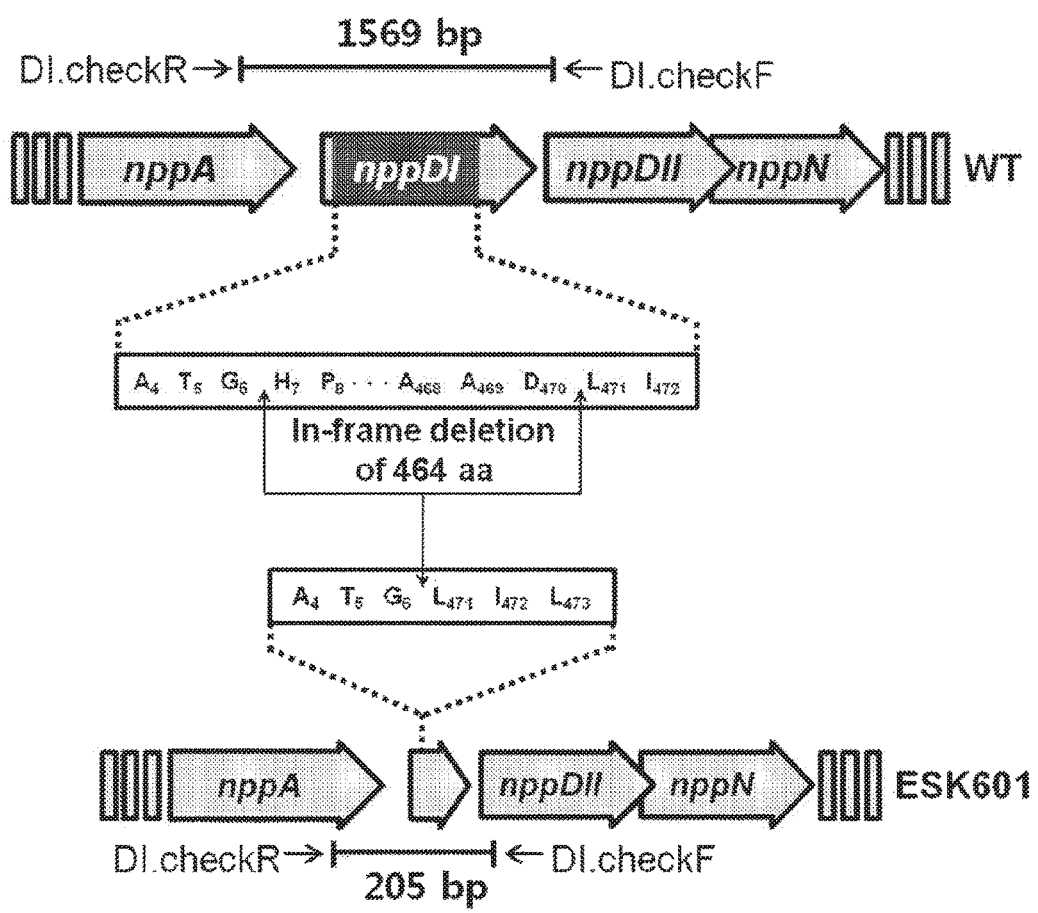
FIG. 2a is a schematic diagram illustrating the in-frame deletion of 464 aa in NppDI to generate ΔnppDI mutant ESK601.

The nppDI gene was disrupted by pKC1139-mediated double crossover recombination. A 2.3 kb BamHI/SpeI fragment, including the nppDI upstream region, was PCR amplified from *P. autotrophica* genomic DNA using the oligonucleotides DI.N.F and DI.N.R. A 1.5 kb SpeI/KpnI fragment, including the nppDI downstream region, was PCR amplified from *P. autotrophica* genomic DNA using the oligonucleotides DI.A.F and DI.A.R. The two resulting PCR products were cloned individually in the T&A cloning vector (RBC), further excised from the resulting constructs with BamHI/SpeI and SpeI/KpnI, respectively, and ligated, with the 7.5 kb BamHI/KpnI fragment from pKC1139-tsr, yielding plasmid pMJDI for the in-frame deletion of nppDI (FIG. 2a).

Figure 2B:
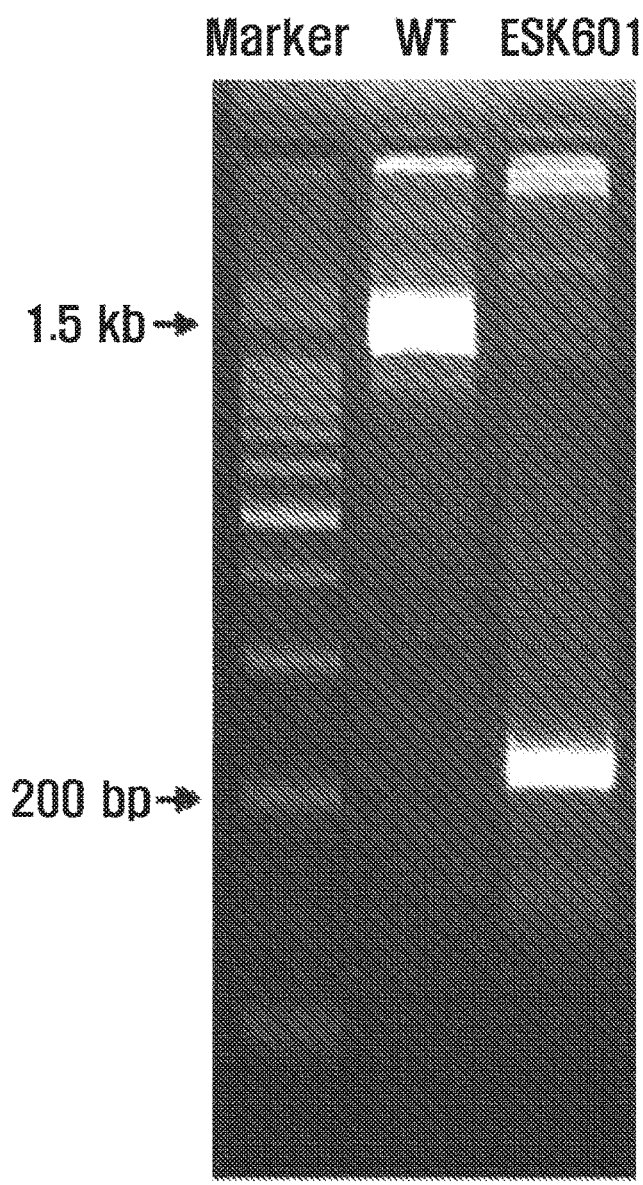
FIG. 2b illustrates the results of PCR analysis of wild-type and mutant genomic DNAs.

The pMJDI was first introduced into *E. coli* ET12567/pUZ8002 via electroporation, followed by introduction into *P. autotrophica* KCTC9441 by conjugation. After incubation at 28° C. for 16 hrs, each plate was overlaid with 1 ml of sterile water containing both thiostrepton and apramycin at the final concentration of 50 μg/ml each. Exconjugants were then further incubated at 37° C. to select homologous recombination. The exconjugants were restreaked on antibiotic-free ISP2 plates selected, and confirmed by PCR amplification using a pair of oligonucleotides DI.checkF-DI.checkR (FIG. 2b).

EXAMPLE 3

Construction of Plasmids pMJPDI and pMJYDI for the Complementation of the nppDI Deletion Mutant ESK601

Figure 3A:
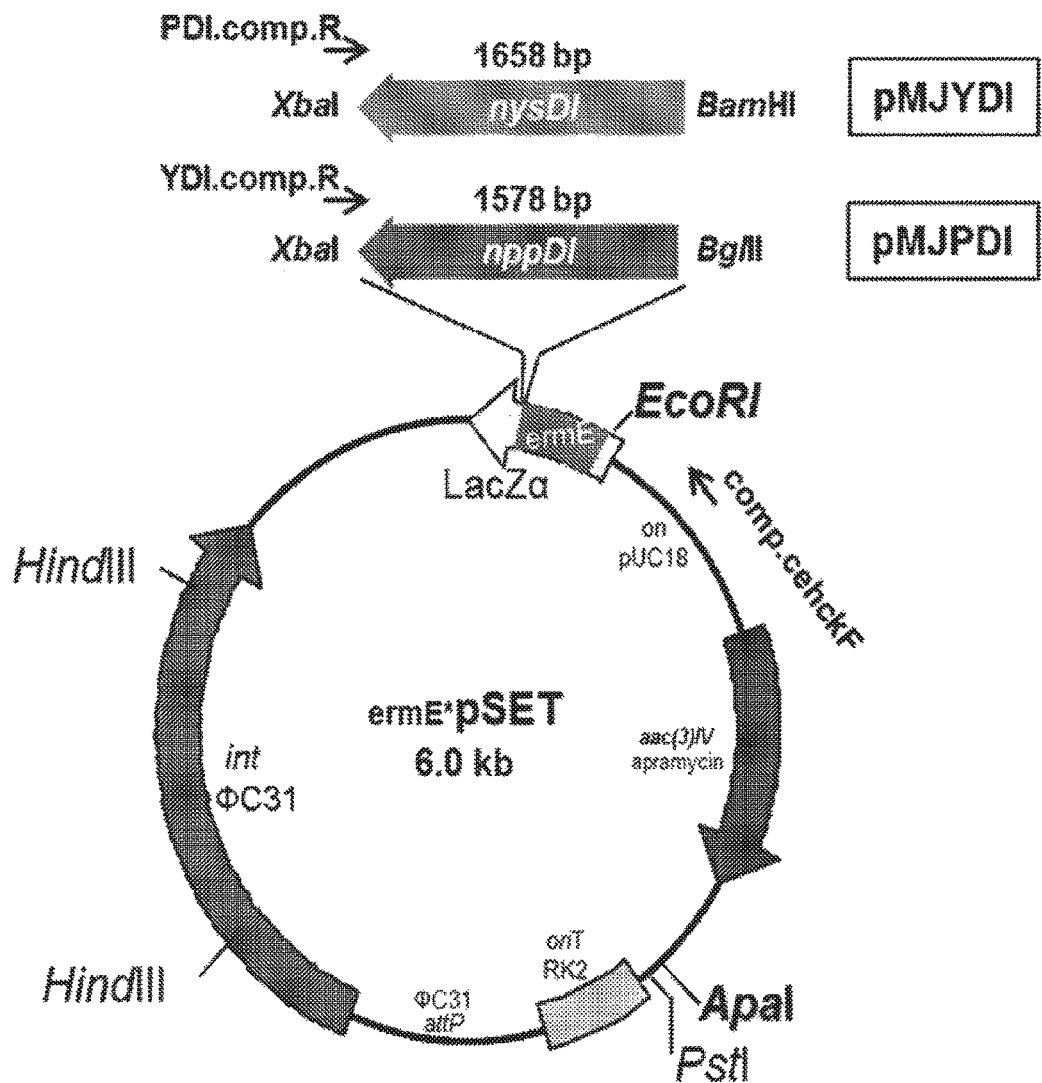
FIG. 3a illustrates the cloning of nppDI and nysDI into the ermE*pSET152 vector.
Figure 3B:
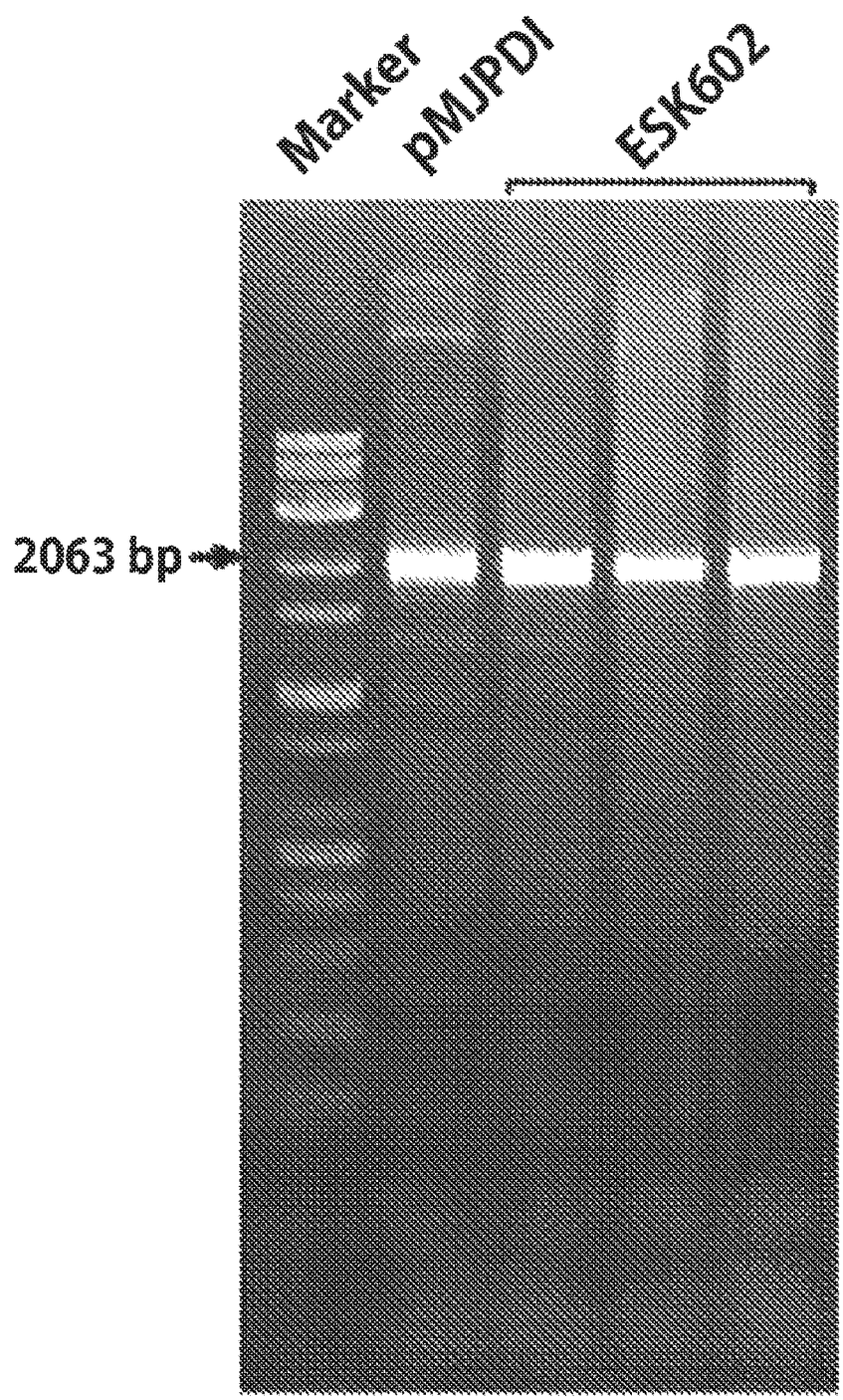
FIG. 3b illustrates the result of PCR with the DNA samples from *Pseudonocardia autotrophica* ESK602 YEME liquid cultures.
Figure 3C:
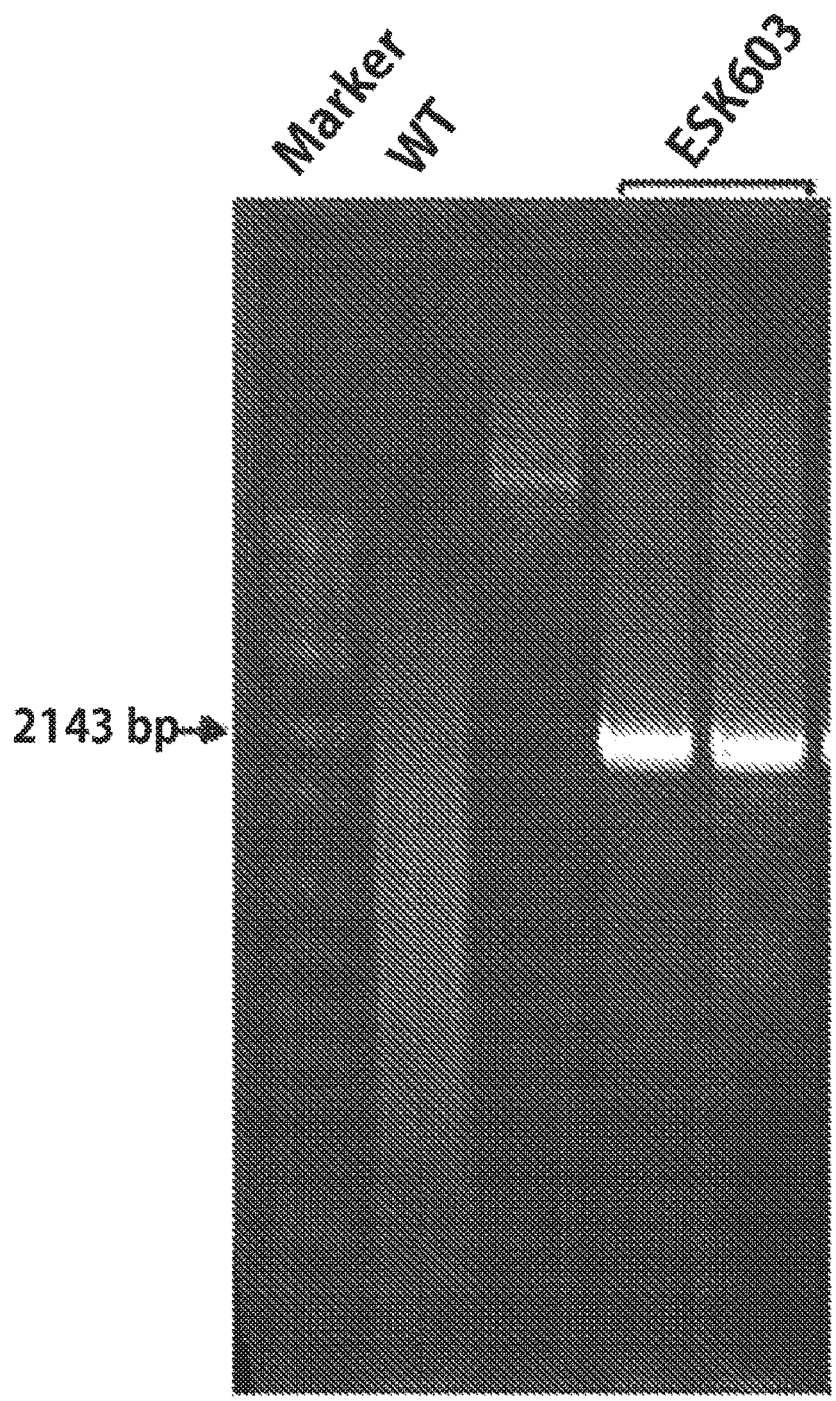
FIG. 3c illustrates the result of PCR with the DNA samples from *Pseudonocardia autotrophica* ESK603 YEME liquid cultures.

A 1578 by fragment encompassing the nppDI coding sequence was PCR amplified from *P. autotrophica* genomic DNA with the oligonucleotides PDI.comp.F and PDI.comp.R. The PCR product was cloned in the RBC T&A cloning vector, sequenced, further excised from the resulting construct as BglII/XbaI fragment, and ligated into the BamHI/XbaI sites of the integrative vector ermE*pSET152, yielding plasmid pMJPDI. A 1658 by fragment containing the nysDI coding sequence was PCR amplified from *S. noursei* genomic DNA using YDI.comp.F and YDI.comp.R. The obtained PCR product was cloned in the RBC T&A cloning vector, sequenced, further excised from the resulting construct as BamHI/XbaI fragment, and ligated into the BamHI/XbaI sites of the integrative vector ermE*pSET152, yielding plasmid pMJYDI. The resulting recombinant plasmids were introduced into the *P. autotrophica* ESK601 mutant strain individually, yielding ESK602 (complemented with pMJPDI) and ESK603 (complemented with pMJYDI) derivatives (FIG. 3b and FIG. 3c).

EXAMPLE 4

Construction of NppC PKS ER Domain Deletion Mutant *Pseudonocardia autotrophica* ESK604

Figure 4A:
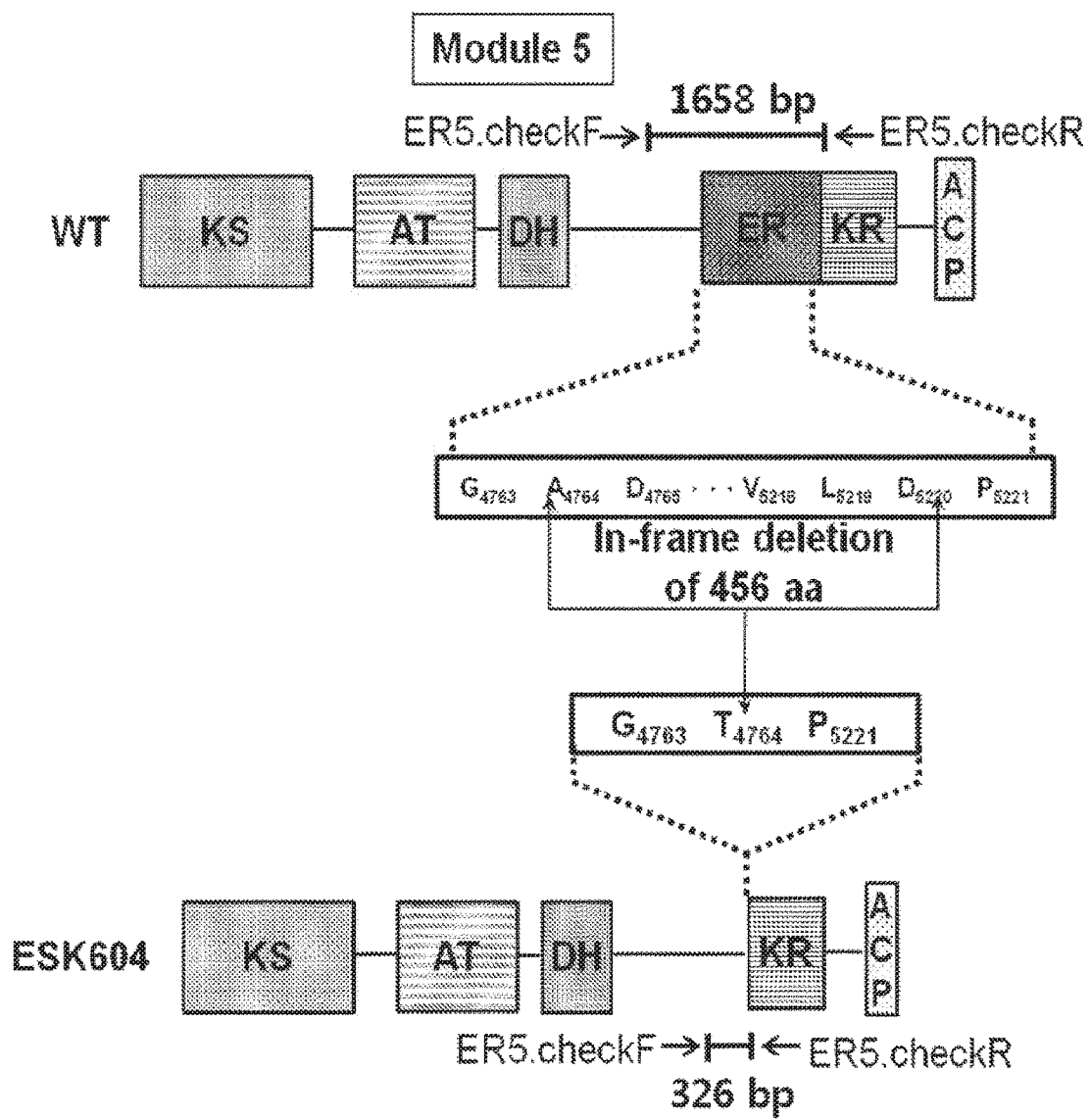
FIG. 4a is a schematic diagram illustrating the in-frame deletion of 456 aa in NppC to generate ΔER5 mutant ESK604.
Figure 4B:
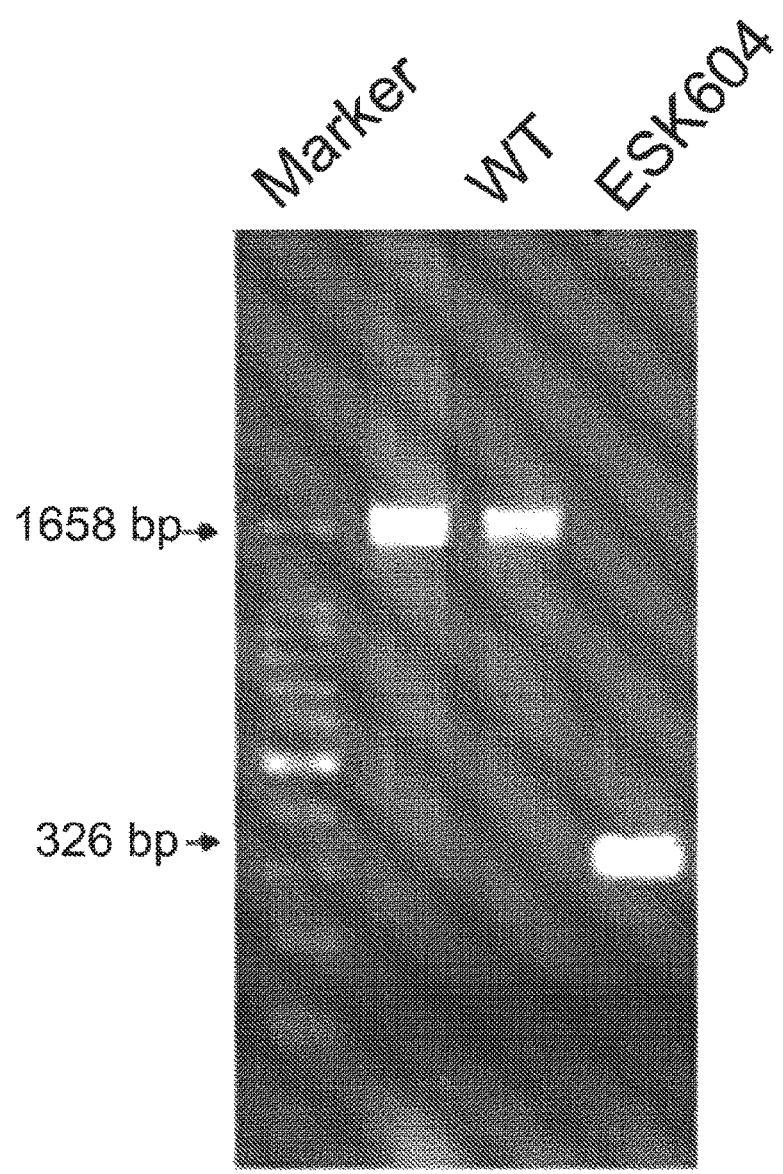
FIG. 4b illustrates the results of PCR analysis of wild-type and mutant genomic DNAs.

To delete the ER5 domain of the NppC PKS by pKC1139-based double homologous recombination, the ER5 domain in-frame deletion plasmid pMJC was prepared by the same manner as described in Example 2, by which exconjugants were selected (FIG. 4a). DNA was extracted therefrom, followed by PCR amplification by using the pair of ER5.checkF-ER5.checkR (FIG. 4b).

EXAMPLE 5

NPP Purification and LC-MS/NMR Analysis

<5-1> NPP Purification

As described hereinbefore, spore suspension in the volume of 10% was inoculated in 10 YEME (yeast extract 3 g, bacto-peptone 5 g, malt extract 3 g, glucose 10 g, sucrose 340 g, and $MgCl_2 \cdot 6H_2O$ 5 mM in 1 L of distilled water), followed by culture for 8 days. The fermentation broth (10 L) was extracted three times with 2.5 L butanol. The organic phase was then combined and concentrated using a vacuum evaporator. The raw extract was dissolved in methanol and separated by column chromatography using silica gel (YMC, 50 mm) with methanol-water (60:40, v/v) mobile phase. Each fraction was analyzed by HPLC and fractions containing NPP were collected, concentrated, re-dissolved in methanol, and loaded onto a size-exclusion column chromatography column (1.2 meter long column packed with Sephadex LH-20). The fractions containing NPP with >95% purity were collected. After removal of methanol by vacuum evaporation, approximately 20 mg of NPP was obtained.

<5-2> NPP Analysis

The LC-MS analysis was performed with an Agilent 1100 series LC/MSD Trap system (Agilent Technologies, Santa Clara, Calif.), using a ZORBAX RX-C18 column (5 μm, 4.6×150 mm, Agilent). The column was equilibrated with 50% solvent A (50 mM ammonium acetate, pH 6.5) and 50% solvent B (Methanol), and developed using the following gradient: 50% B (0 min), 90% B (21 min), 100% B (25 to 30 min), 50% B (33 to 35 min) at a flow rate of 0.6 ml/min and UV/vis detection at 380 nm. The mass spectrometer was run in positive ion detection mode and set to scan between 100 and 1500 m/z. The NMR data were recorded on a Bruker NMR spectrometry (500 MHz).

<5-3> NPP Analysis Result

1) The Purified NPP is a Nystatin-Like Tetraene Polyene Bearing a Disaccharide mycosamine(α1-4)-N-acetyl-glucosamine.

The UV/Vis absorption profile of NPP was also consistent with nystatin. The $^1$H-NMR and $^{13}$C-NMR spectra contains 12 proton signals ($\delta_H$: 5.39-6.20 ppm) typical of double bonds and the corresponding carbon atoms ($\delta_C$: 129.4-135.4 ppm), suggesting that NPP is a nystatin-like polyene compound (FIG. 1a). However, the high resolution ESI-MS analysis showed that the exact mass of NPP is 1129.6006 $[C_{55}H_{89}N_2O_{22}]^+$ (cacld. 1129.5901), which is larger than nystatin by 203 Da. Using 1D and 2D NMR techniques, including DEPT, $^1$H-$^1$H COSY, HSQC, and HMBC, the structure of NPP was determined to be the one of FIG. 1a.

The $^1$H and $^{13}$C chemical shifts of compound 1 and compound 2 measured by 500 MHz spectrometer were presented in Table 3 (DMSO-d6) and Table 4 ($CD_3OD$). The proton signal at $\delta_H$ 7.81 (d, J=7.5 Hz, $^1$H) in $^1$H NMR spectrum (DMSO-d6) disappeared when $D_2O$ was added. No correlation of this proton to any carbon was found in the HSQC spectrum. These results indicated the presence of an amide proton. In comparison to the reported NMR data for amphotericin A, the obvious difference is that the presence of an acetyl group is observed, which was supported by the observation of a singlet methyl proton signal at $\delta_H$ 1.79, the corresponding carbon signals at $\delta_C$ 23.0 for the methyl carbon and 169.0 for carbonyl carbon.

Figure 1B:
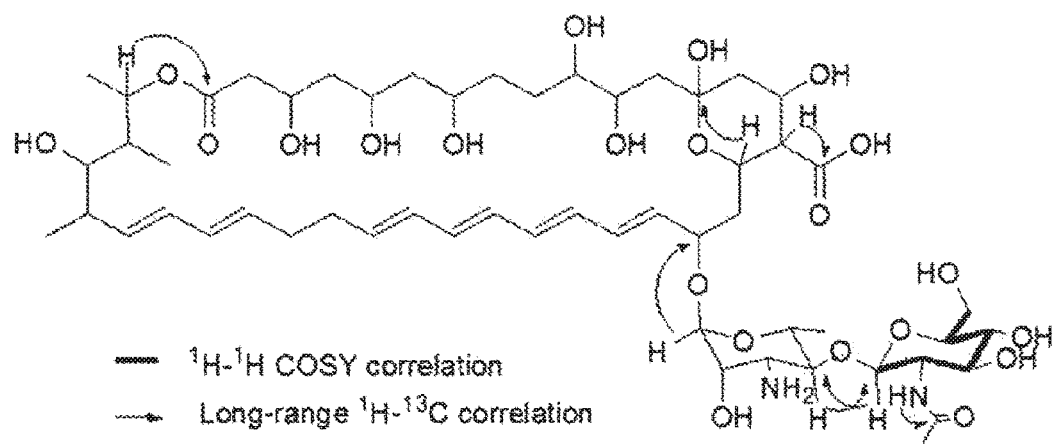

The correlation between the proton ($\delta_H$ 7.81) and the carbon ($\delta_C$ 169.0) confirmed the existence of an N-acetyl group. The other significant difference includes the presence of a doublet proton signal at $\delta_H$ 4.35 (d, J=8.0 Hz, $^1$H), which was determined to be an anomeric proton of N-acetyl-glucosamine in the $^1$H-$^1$H COSY analysis (FIG. 1b), along with HSQC and HMBC. The attachment of N-acetyl-glucosamine to mycosamine at the 4'-position to form a disaccharide was verified by the chemical shift of C-4' to 82.4 ppm and the correlations between H-1" and C-4', as well as H-4' and C-1" (FIG. 1b). Therefore, NPP was determined to include tetraene polyene macrolactone core identical to nystatin bearing a disaccharide formed from the 1-44 linkage of N-acetyl-glucosamine to mycosamine.

TABLE 3

| Position | Chemical shift (ppm)[a] | | proton | Chemical shift (ppm) | |
|---|---|---|---|---|---|
| | $^1$H NMR | $^{13}$C NMR | | $^1$H NMR | $^{13}$C NMR |
| 1 | | 170.4 | 32 | 5.96 | 129.4 |
| 2 | 2.33 | 42.5 | 33 | 5.51 | 135.4 |
| 3 | 4.02 | 65.7 | 34 | 2.24 | 40.4 |
| 4 | 1.50 | 44.3 | 35 | 3.15 | 75.6 |
| 5 | 3.80 | 67.9 | 36 | 1.79 | 39.9 |
| 6 | 1.36-1.42 | 44.3 | 37 | 5.07 | 70.3 |
| 7 | 3.59 | 69.4 | 38 | 1.11 | 16.6 |
| 8 | 1.36-1.46 | 28.4 | 39 | 0.87 | 12.0 |
| 9 | 1.38 | 34.5 | 40 | 0.97 | 16.9 |
| 10 | 3.22 | 73.3 | 41 | | 172.0[b] |
| 11 | 3.90 | 70.2 | 1' | 4.46 | 97.1 |
| 12 | 1.55-1.68 | 42.2 | 2' | 3.73 | 68.7 |
| 13 | | 97.5 | 3' | 2.78 | 54.6 |
| 14 | 1.16, 1.88 | 44.3 | 4' | 3.16 | 82.4 |
| 15 | 3.99 | 65.9 | 5' | 3.15 | 76.7 |
| 16 | 1.88 | 57.8 | 6' | 1.16 | 17.5 |
| 17 | 3.98 | 65.5 | 1" | 4.36 | 102.0 |
| 18 | 1.70, 1.78 | 37.5 | 2" | 3.40 | 55.7 |
| 19 | 4.32 | 75.5 | 3" | 3.40 | 73.7 |
| 20 | 5.74 | 134.2 | 4" | 3.06 | 70.5 |
| 27 | 5.68 | 134.2 | 5" | 3.15 | 71.3 |
| 28 | 2.18 | 31.8[a] | 6" | 3.45, 3.75 | 61.0 |
| 29 | 2.18 | 31.6[a] | $COCH_3$ | 1.79 | 23.0 |
| 30 | 5.51 | 131.2 | CO | | 169.0 |
| 31 | 5.96 | 131.1 | | | |

[a] the double-bond proton signals for 21 through 26 were highly overlapped and hard to be assigned.
[b] Exchangeable assignments

TABLE 4

| Position | Chemical shift (ppm)[a] | | Position | Chemical shift (ppm) | |
|---|---|---|---|---|---|
| | $^1$H NMR | $^{13}$C NMR | | $^1$H NMR | $^{13}$C NMR |
| 1 | | 173.0 | 19 | 4.38 | 71.4 |
| 2 | 2.44 | 43.9 | 20 | 5.69 | 136.7 |
| 3 | 4.20 | 68.6 | 27 | 5.67 | 135.7 |
| 4 | 1.62 | 45.2 | 28 | 2.20 | 33.7 |
| 5 | 4.01 | 70.8 | 29 | 2.20 | 33.7 |
| 6 | 1.47 | 45.2 | 30 | 5.54 | 133.0 |
| 7 | 3.78 | 72.2 | 31 | 5.97 | 132.9 |
| 8 | 1.42 | 39.0[b] | 32 | 6.02 | 131.9 |
| 9 | 1.44 | 39.5[b] | 33 | 5.47 | 136.3 |
| 10 | 1.44, 1.52 | 38.8[b] | 34 | 2.40 | 42.3 |
| 11 | 4.17 | 68.5 | 35 | 3.28 | 78.8 |
| 12 | 1.66 | 48.0 | 36 | 1.92 | 42.1 |
| 13 | | 99.2 | 37 | 5.20 | 73.3 |
| 14 | 1.32, 2.04 | 45.1 | 38 | 1.19 | 17.4 |

TABLE 4-continued

| Chemical shift (ppm)[a] | | | Chemical shift (ppm) | | |
|---|---|---|---|---|---|
| Position | $^1$H NMR | $^{13}$C NMR | Position | $^1$H NMR | $^{13}$C NMR |
| 15 | 4.24 | 67.8 | 39 | 0.96 | 12.9 |
| 16 | 2.14 | 59.1 | 40 | 1.04 | 17.5 |
| 17 | 4.15 | 69.4 | 41 |  | 177.0 |
| 18 | 1.77, 1.86 | 42.4 |  |  |  |

[a] the double-bond proton signals for 21 through 26 were highly overlapped and hard to be assigned.
[b] Exchangeable assignments 2) Inactivation of nppDI in *Pseudonocardia Autotrophica* Leads to the Production of NPP Aglycone Identical to Nystatinolides.

The NPP structure represents a polyene macrolide with a 38-membered macrolactone ring, identical to nystatin aglycone (nystatinolide), and a disaccharide moiety attached at the C-19 position. The NPP biosynthetic gene cluster, which is highly homologous previously identified nystatin biosynthetic genes, contained a 1470 by-nppDI gene encoding a glycosyltransferase, which is presumed to be responsible for the attachment of the sugar moiety to the NPP aglycone at the C-19 hydroxyl.

To confirm the role of NppDI in mycosamine attachment, an in-frame deletion mutant of nppDI was constructed by removing a 1392 by internal region of nppDI in *P. autotrophica* using the temperature-sensitive suicide vector pKC1139-tsr (FIG. 2a) resulting in recombinant strain ESK601. The deletion in the nppDI gene eliminated 464 out of 489 amino acids from the corresponding NppDI protein. DNA sequence analysis of the chromosomal DNA regions flanking the deletion in the ESK601 strain verified the expected mutation, and confirmed that no unexpected lesions were introduced during the gene replacement procedure (FIG. 2b).

Figure 5:
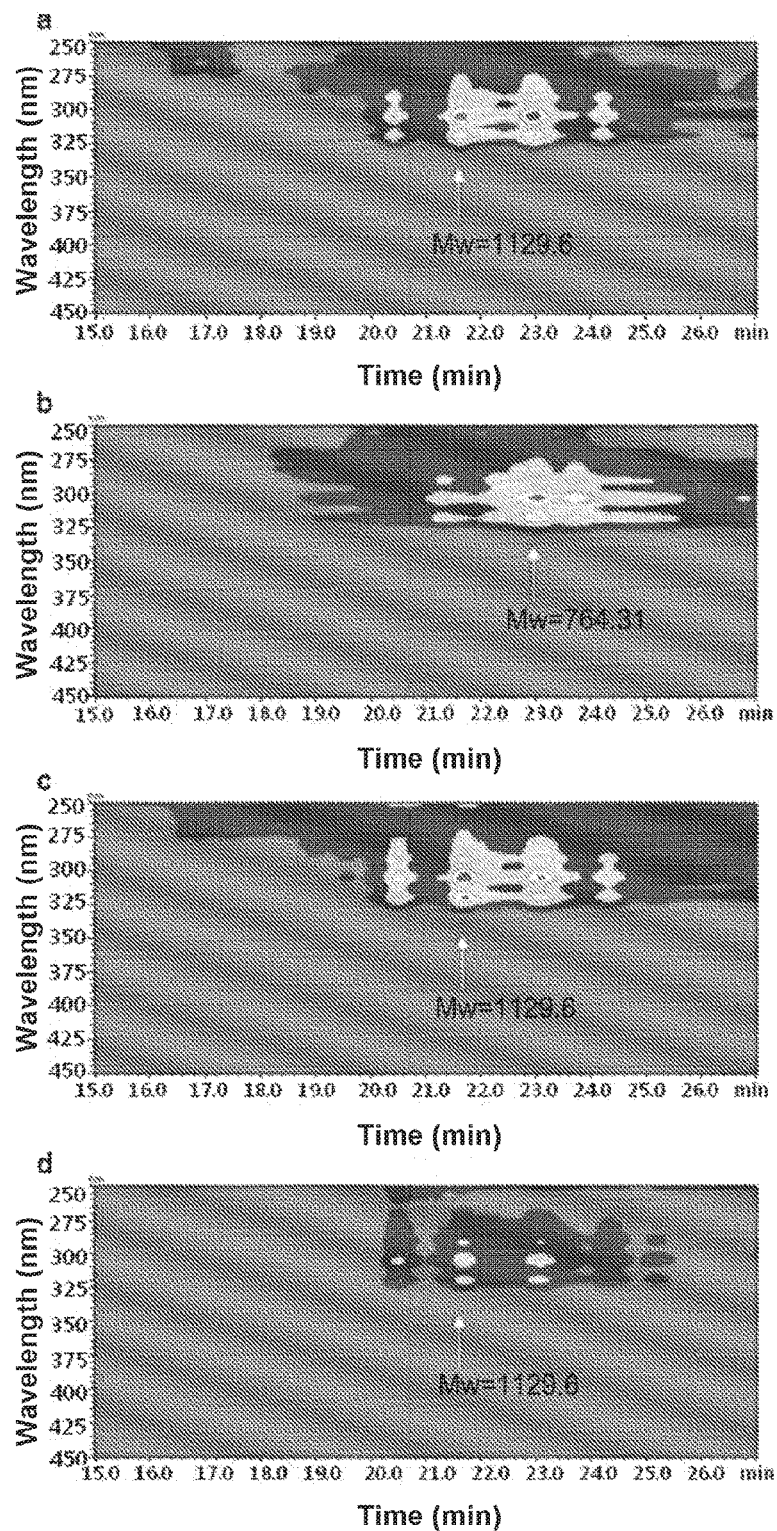
FIG. 5 illustrates the results of analysis with the metabolites produced by *Pseudonocardia autotrophica* wild-type and the mutants thereof, ESK601, ESK602, and ESK603, in which a indicates the wild-type, b indicates ESK601, c indicates ESK602, and d indicates ESK603.

In order to analyze polyene macrolide production by the ESK601 mutant, the strain was cultured for 8 days and the media extracts were analyzed for the presence of NPP-related polyene macrolides using a diode array detector (DAD)-HPLC. Several independent clones for each mutant were employed in this analysis. Compound 3 (FIG. 1a) was accumulated in ESK601, and its structure was characterized via LC-MS and NMR analysis. The LC-MS spectrum contained a signal at m/z 763.31 for $[C_{41}H_{63}O_{14}]$ (calculated mass 763.43) (FIG. 5b).

Using this analysis, the mass of this compound was shown to be smaller than compound 1 (FIG. 1a) by 364 Da, indicating that both the disaccharide and oxygen atom were missing from the aglycone. To confirm the structure, a large-scale preparation of aglycone 3 was conducted in 10 L fermentation. After purification and preparation of the compounds 1 and 3 (8 mg), structural analysis was performed including $^1$H NMR, $^{13}$C NMR, DEPT, $^1$H-$^1$H COSY, HSQC, and HMBC. The proton and carbon chemical shifts of compound 3 were assigned (Table 3) based on the assignments of the chemical shifts of proton and carbon atoms in compound 1. Except for the hydroxyl group at the C-10 position, which is believed to be catalyzed by a P450 monooxygenase, all the hydroxyl groups introduced by the PKS assembly line were confirmed as expected. Along with the MS and NMR analyses, the compound accumulated in the ESK601 mutant lacked both the C-10 hydroxyl and the C-19 disaccharide moieties (FIG. 1). This analysis revealed that the disaccharide moiety was not present in compound 3, and thus NppL might n of be able to hydroxylate NPP at the C-10 position. This observation is consistent with previous findings that glycosylation with mycosamine normally precedes C-10 hydroxylation in nystatin biosynthesis, as well as C-8 hydroxylation in amphotericin biosynthesis. Thus NppL might not be able to hydroxylate NPP aglycone at the C-10 position.

3) Expression of nppDI or nysDI in the ESK601 Mutant Restored NPP Production.

To confirm that NppDI is indeed responsible for glycosylation of the NPP aglycone, the present inventors performed trans-complementation of the ESK601 mutant by expressing nppDI under the control of the ermE*p promoter. For these experiments, the inventors used the integrating conjugative vector ermE*pSET152, into which the coding region of nppDI was cloned, resulting in pMJPDI (FIG. 3a). The plasmid was introduced into *P. autotrophica* ESK601 by conjugation, and the resulting *P. autotrophica* ESK602 strain was confirmed by PCR analysis (FIG. 3b).

DAD-HPLC-MS analysis demonstrated that NPP production was restored in the ESK602 mutant strain (FIG. 5c), indicating that the absence of NPP from ESK601 was due to a lack of the nppDI gene.

Further characterization of the nppDI gene product via database-assisted in silico analysis revealed that it encodes a 489 aa-containing protein, showing 82% and 78% amino acid identities to glycosyltransferases NysSI from nystatin-producing *S. noursei* and AmphDI from amphotericin-producing *S. nodosus*, respectively.

Since the NPP and nystatin gene clusters contain the glycosyltransferase genes nppDI and nysDI, respectively, the C-19 disaccharide glycosylation of NPP by NppDI or sequentially by NppDI and another unknown glycosyltransferases needed to be verified. The ESK601 mutant was complemented with the nysDI cloned under the control of the ermE*p promoter in ermE*pSET152, yielding plasmid pMJYDI (FIG. 3a). The plasmid was introduced into the ESK601 mutant strain resulting ESK603 (FIG. 3c). DAD-HPLC-MS analysis confirmed that complementation of the ESK601 mutant with the construct pMJYDI (ESK603) restored the wild type production pattern of compound 1 (FIG. 5d).

These results indicate that the glycosylation function of NppDI could be substituted by NysDI, which transfers the mycosamine to the C-19 position. Therefore, the additional attachment of N-acetyl-glucosamine in NPP is believed to be proceeded by another glycosyltransferase present outside of the NPP biosynthetic gene cluster.

4) Inactivation of the ER Domain of NppC in *Pseudonocardia autotrophica* Leads to the Production of Heptaene NPP Derivatives.

Figure 1C:
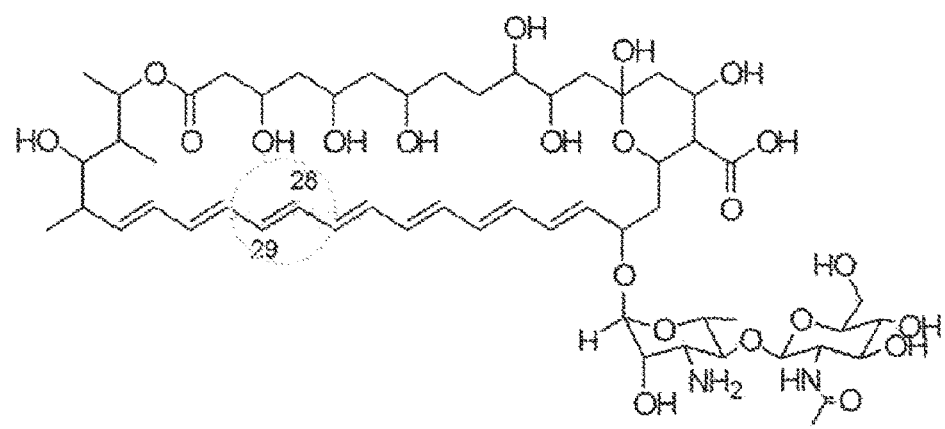
Figure 6:
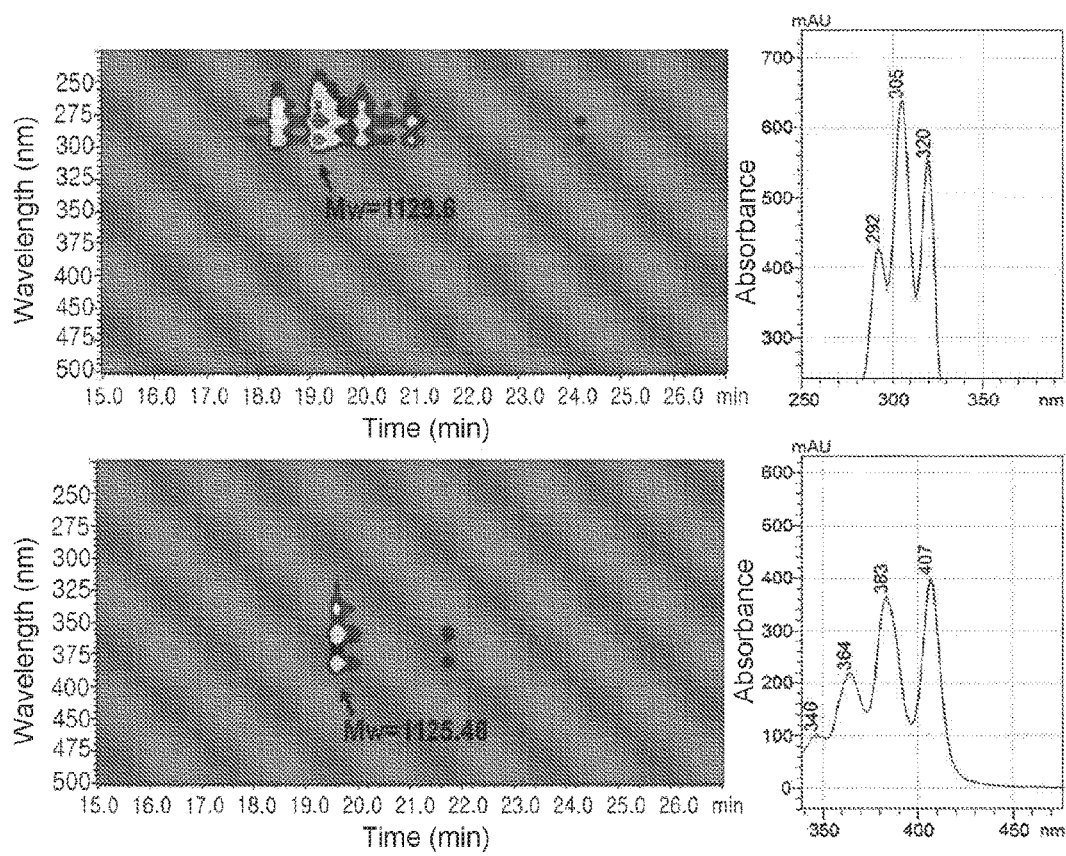
FIG. 6 illustrates the results of analysis with the metabolites produced by *Pseudonocardia autotrophica* wild-type (a) and the mutant thereof, ESK604 (b).
Figure 7:
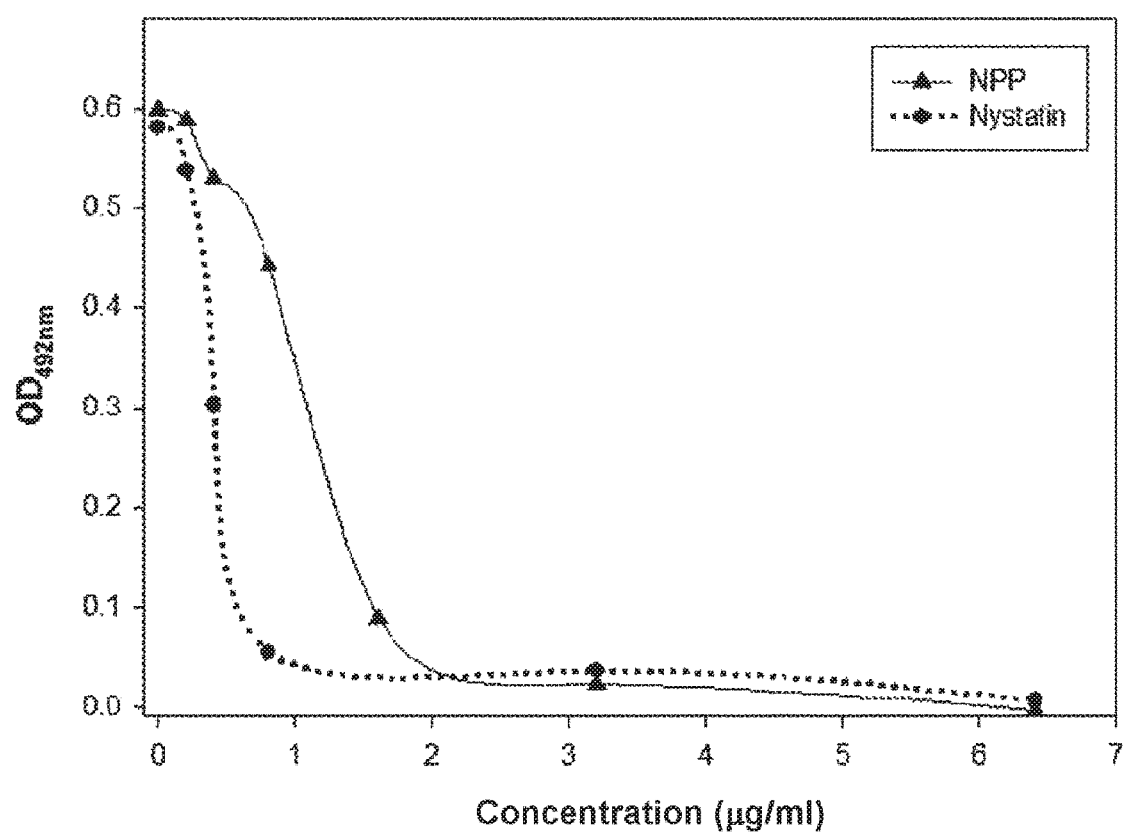
FIG. 7 illustrates the regression curve to calculate the antifungal activities of NPP and nystatin.
Figure 8:
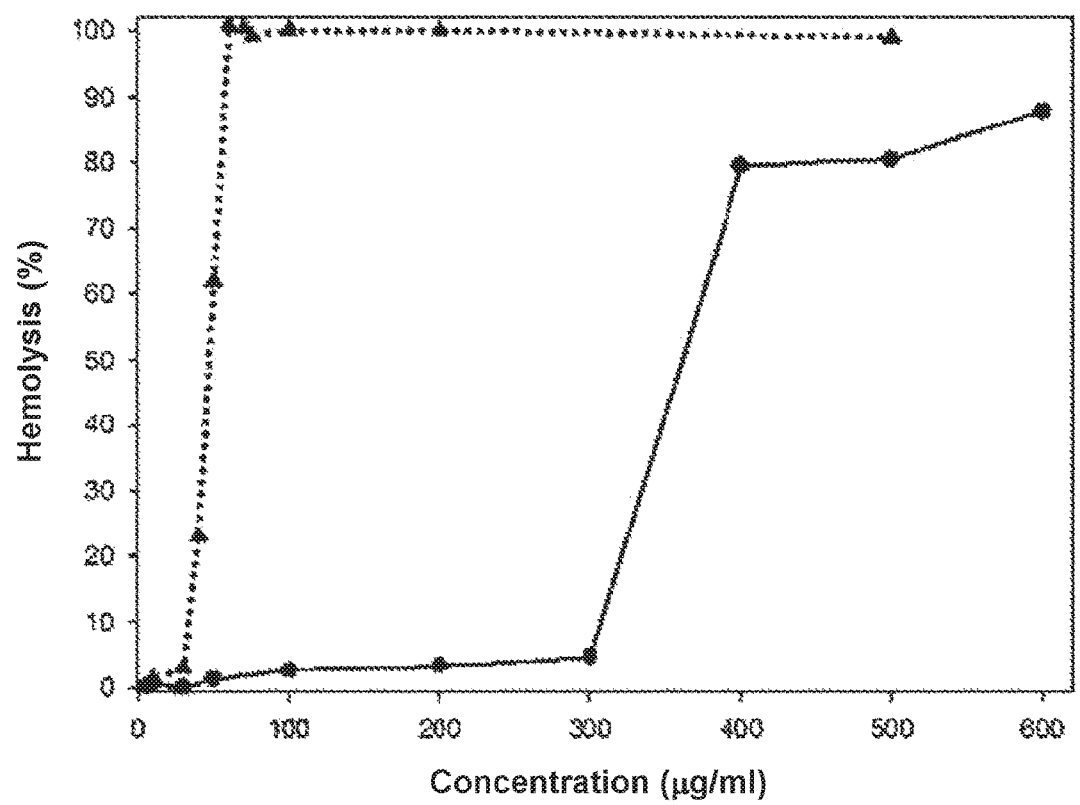
FIG. 8 illustrates the regression curve to calculate the hemolytic activities of NPP and nystatin.

Polyene production by the ESK 604 mutant constructed in Example 4 was analyzed by HPLC-DAD-MS and UV absorbance assay. As a result, NPP of compound 1 was not produced in the ESK 604 strain. But heptaene NPP derivatives were produced therein. The exact mass of the heptaene was $1125.46[C_{55}H_{86}N_2O_{22}]^-$ (calcd. 1125.57), which was measured by high performance ESI-MS. This result indicates that the heptaene was the heptaene derivative of NPP with a double bond between C-28 and C-29 (FIG. 1c and FIG. 6).

EXAMPLE 6

Solubility Measurement

The polyene region of nystatin is extremely non-polar, which is presumed to promote hydrophobic interactions with sterols within the fungal cell membrane, and orients the polyol component of the molecule toward the internal aqueous channel. However, this low polarity also leads to significant difficulties in administration during human therapy. To investigate the effect of the additional N-acetyl-glucosamine moiety, the present inventors tested the solubility of the purified NPP as well as the nystatin A1 as a reference in an aqueous buffer solution of 10 mmol Tris-HCl (pH 7.0) using spectrophotometric methods.

Particularly, stock solutions of nystatin A1 (Sigma, N6261) standard (1.2 mg/ml) and the purified NPP (12 mg/ml) were prepared in methanol. A 100 µl portion of each stock was freeze-dried under vacuum for 24 h. Either 50 µl (nystatin A1) or 2 µl (NPP) of aqueous 10 mmol Tris-HCl buffer (pH 7.0) was added to the dry polyenes, and the solution was saturated by extensive (>15 min) vortexing. After centrifugation, polyene concentrations in the solution were determined by measuring UV absorbance spectra on SHIMADZU UV-1601 UV/Vis spectrophotometer after appropriate dilution. Specifically, the characteristic tetraene UV peak at 306 nm was used for quantification with experimentally determined extinction coefficients (J. Med. Chem. 49:2431-2439, 2006).

As a result, the solubility of nystatin A1 and NPP were found to be 0.11 mg/ml and 34.7 mg/ml, respectively. Thus, NPP containing the additional N-acetyl-glucosamine moiety displayed more than 300-fold higher water solubility than nystatin A1. Therefore, it was confirmed that additional N-acetyl-glucosamine moiety in NPP was significantly increased its water solubility.

EXAMPLE 7

Antifungal Activity Analysis

The test organism used for the polyene macrolide bioactivity assays was *Candida albicans* ATCC 10231, which was grown in 120 µl of YM medium without NaCl (with an inoculum of 1,000 CFU per well) and 30 µl of diluted polyene macrolide samples. The antibiotics were diluted in methanol in series to ensure that concentrations resulting in no inhibition to complete inhibition of the growth of the test organism were used. The test organism cultures with diluted antibiotics were then incubated in 96-well microtiter plates at 30° C. without shaking. After 12, 14, and 16 h, growth was measured based on the optical density at 492 nm using a TECAN Infinite F50 microtiter plate reader. The optical density was plotted against the antibiotic concentration, and the MIC at which 50% of isolates are inhibited ($MIC_{50}$) was estimated from the regression curve at 50% growth inhibition.

As a result, the $MIC_{50}$ for NPP was shown to be 1.08 µg/ml, while the $MIC_{50}$ for nystatin was found to be 0.43 µg/ml under the same conditions, suggesting that the antifungal activity of NPP is approximately 2-fold lower but still maintained.

EXAMPLE 8

In Vitro Measurement of Hemolytic Activity

The hemolytic assay for the polyene macrolides was performed by monitoring the ability of the macrolides to cause lysis of erythrocytes in defibrinated horse blood (Gene. 111:61-68, 1992). Samples (0.1 ml) with different polyene macrolide concentrations (10 to 500 µg/ml in DMSO) were prepared from stock solutions of the purified polyenes (5 mg/ml in DMSO). The diluted samples were mixed with 0.9 ml horse blood-phosphate-buffered saline (PBS), which consisted of PBS buffer containing 2.5% defibrinated horse blood (KisanBiotech, Korea), and incubated in a water bath at 37° C. Samples were collected at 30 min, centrifuged at 5,000 rpm for 5 min, and the $OD_{540}$ was measured. One hundred percent hemolysis was defined as the $OD_{540}$ value obtained from a suspension of 2.5% horse blood in distilled water, and 0.9 ml horse blood-PBS with the addition of 0.1 ml DMSO was used as a blank. Each experiment was performed in triplicate, and samples containing nystatin were used as standards.

As a result, the $HC_{50}$ for NPP was 403.7 µg/ml, while the $HC_{50}$ for nystatin in the same experiment was 33 µg/ml. The hemolytic activity of NPP was therefore more than 10-fold lower. These results demonstrate that the additional N-acetyl-glucosamine moiety significantly reduces hemolytic activity of polyene macrolide antibiotics.

TABLE 5

|  | nystatin | NPP | Fold (NPP/nystatin) |
| --- | --- | --- | --- |
| Solubility (mg/ml) | 0.11 ± 0.03 | 4.7 ± 0.45 | 315.5 |
| Antifungal activity ($IC_{50}$, µg/ml) | 0.43 ± 0.02 | 1.08 ± 0.06 | 2.5 |
| Hemolytic activity ($HC_{50}$, µg/ml) | 33 ± 0.54 | 403.7 ± 0.97 | 12.2 |

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

SEQUENCE LISTING

<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: DI.N.F

<400> SEQUENCE: 1
ggatccggtc gaacagcgtg                                              20

<210> SEQ ID NO 2
<211> LENGTH: 20
<212> TYPE: DNA
<213> ORGANISM: Artificial Sequence

<220> FEATURE:
<223> OTHER INFORMATION: DI.N.R

<400> SEQUENCE: 2
actagtctga tcctgcgcct                                                     20

<210> SEQ ID NO 3
<211> LENGTH: 22
<212> TYPE: DNA
<213> ORGANISM: Artificial Sequence
<220> FEATURE:
<223> OTHER INFORMATION: DI.A.F

<400> SEQUENCE: 3
actagtaccc gtcgcgtggc gc                                                  22

<210> SEQ ID NO 4
<211> LENGTH: 21
<212> TYPE: DNA
<213> ORGANISM: Artificial Sequence
<220> FEATURE:
<223> OTHER INFORMATION: DI.A.R

<400> SEQUENCE: 4
ggtaccgctg atcccgaacg a                                                   21

<210> SEQ ID NO 5
<211> LENGTH: 18
<212> TYPE: DNA
<213> ORGANISM: Artificial Sequence
<220> FEATURE:
<223> OTHER INFORMATION: DI.checkF

<400> SEQUENCE: 5
tgacgtagtc gagctcgt                                                       18

<210> SEQ ID NO 6
<211> LENGTH: 18
<212> TYPE: DNA
<213> ORGANISM: Artificial Sequence
<220> FEATURE:
<223> OTHER INFORMATION: DI.checkR

<400> SEQUENCE: 6
atcaactacc tgatcgct                                                       18

<210> SEQ ID NO 7
<211> LENGTH: 23
<212> TYPE: DNA
<213> ORGANISM: Artificial Sequence
<220> FEATURE:
<223> OTHER INFORMATION: PDI.comp.F

<400> SEQUENCE: 7
agatctaccg aggactaggg att                                                 23

<210> SEQ ID NO 8
<211> LENGTH: 23
<212> TYPE: DNA
<213> ORGANISM: Artificial Sequence
<220> FEATURE:
<223> OTHER INFORMATION: PDI.comp.R

<400> SEQUENCE: 8
tctagatgac tccctggttc ggt                                                 23

<210> SEQ ID NO 9
<211> LENGTH: 22
<212> TYPE: DNA
<213> ORGANISM: Artificial Sequence
<220> FEATURE:
<223> OTHER INFORMATION: YDI.comp.F

<400> SEQUENCE: 9
ggatccacgg gcattggcca ca                                              22

<210> SEQ ID NO 10
<211> LENGTH: 23
<212> TYPE: DNA
<213> ORGANISM: Artificial Sequence
<220> FEATURE:
<223> OTHER INFORMATION: YDI.comp.R

<400> SEQUENCE: 10
tctagagtca gtcggttgcc agg                                             23

<210> SEQ ID NO 11
<211> LENGTH: 18
<212> TYPE: DNA
<213> ORGANISM: Artificial Sequence
<220> FEATURE:
<223> OTHER INFORMATION: Comp.checkF

<400> SEQUENCE: 11
tgcagctggc acgacagg                                                   18

<210> SEQ ID NO 12
<211> LENGTH: 20
<212> TYPE: DNA
<213> ORGANISM: Artificial Sequence
<220> FEATURE:
<223> OTHER INFORMATION: ER5.AT.F

<400> SEQUENCE: 12
tcgagtcctg ggggatccgt                                                 20

<210> SEQ ID NO 13
<211> LENGTH: 21
<212> TYPE: DNA
<213> ORGANISM: Artificial Sequence
<220> FEATURE:
<223> OTHER INFORMATION: ER5.DH.R

<400> SEQUENCE: 13
ccgtgtcggt accttcaccg t                                               21

<210> SEQ ID NO 14
<211> LENGTH: 20
<212> TYPE: DNA
<213> ORGANISM: Artificial Sequence
<220> FEATURE:
<223> OTHER INFORMATION: ER5.ER.F

<400> SEQUENCE: 14
gtgggtaccc cgctgccggt                                                 20

<210> SEQ ID NO 15
<211> LENGTH: 19
<212> TYPE: DNA
<213> ORGANISM: Artificial Sequence
<220> FEATURE:
<223> OTHER INFORMATION: ER5.KS.R

```
<400> SEQUENCE: 15
agccctctct agagtcgcc                                            19

<210> SEQ ID NO 16
<211> LENGTH: 21
<212> TYPE: DNA
<213> ORGANISM: Artificial Sequence
<220> FEATURE:
<223> OTHER INFORMATION: ER5.checkF

<400> SEQUENCE: 16
actgttcgcg ctcgactgga c                                         21

<210> SEQ ID NO 17
<211> LENGTH: 21
<212> TYPE: DNA
<213> ORGANISM: Artificial Sequence
<220> FEATURE:
<223> OTHER INFORMATION: ER5.checkR

<400> SEQUENCE: 17
tggtcagcag cagatgccgc a                                         21
```

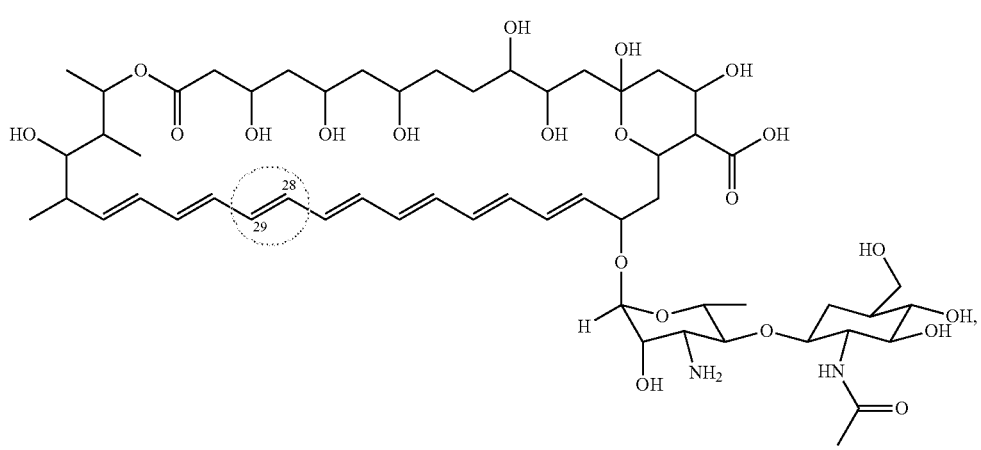

from the strain culture
wherein,
the *Pseudonocardia autotrophica* strain is KCTC9441, and the strain is the one wherein the ER5 domain of nppC PKS gene has been deleted.
4. An antifungal agent containing the polyene compound represented by the formula 4:
[Formula 4]
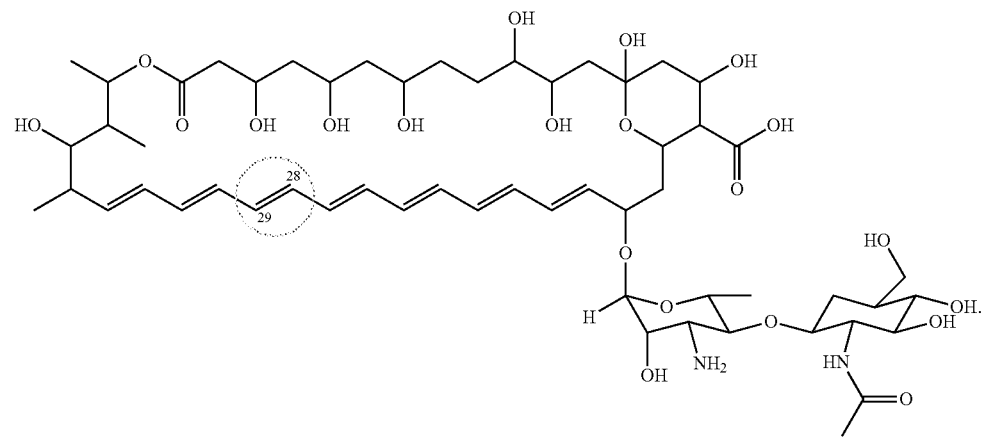

The invention claimed is:

1. A polyene compound represented by the following formula 4:

[Formula 4]

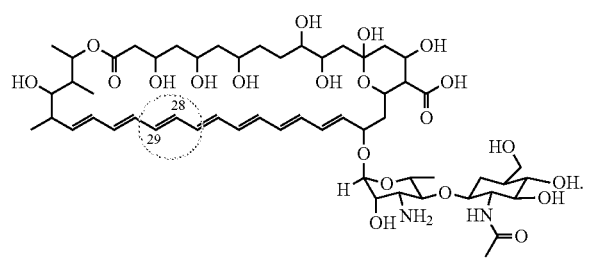

2. The polyene compound according to claim 1, wherein the polyene compound is isolated from *Pseudonocardia autotrophica* KCTC9441.

3. A method for preparing the polyene compound of formula 4 comprising the following steps:

culturing a *Pseudonocardia autotrophica* strain; and isolating the polyene compound represented by the formula 4

[Formula 4]